United States Patent
Beard et al.

(12) 
(10) Patent No.: US 6,884,820 B2
(45) Date of Patent: Apr. 26, 2005

(54) 5,6,7,8-TETRAHYDRONAPHTHALEN-2-YL-7-FLUOROALKYL-HEPTATRIENOIC ACID DERIVATIVES HAVING SERUM GLUCOSE REDUCING ACTIVITY

(75) Inventors: Richard L. Beard, Newport Beach, CA (US); Haiqing Yuan, Irvine, CA (US); Roshantha A. Chandratratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 110 days.

(21) Appl. No.: 10/406,170

(22) Filed: Apr. 3, 2003

(65) Prior Publication Data

US 2004/0198825 A1 Oct. 7, 2004

(51) Int. Cl.$^7$ .................... A01N 37/10; A61K 31/235; C07C 69/76; C07C 62/06; C07C 62/12
(52) U.S. Cl. .................... 514/532; 514/569; 560/56; 562/466; 562/472
(58) Field of Search .................... 514/532, 533, 514/569; 560/56; 562/466, 472

(56) References Cited

U.S. PATENT DOCUMENTS

| 5,455,265 A | 10/1995 | Chaudraratna |
| 5,721,103 A | 2/1998 | Boehm et al. |
| 5,801,253 A | 9/1998 | Klaus et al. |
| 6,114,533 A | 9/2000 | Vullgonda et al. |
| 6,326,397 B1 | 12/2001 | Bollag et al. |
| 6,759,547 B1 * | 7/2004 | Beard et al. .................... 560/56 |

FOREIGN PATENT DOCUMENTS

| WO | WO-93-11755 | 6/1993 |
| WO | WO-97-12853 | 4/1997 |
| WO | WO-01-19770 | 3/2001 |

OTHER PUBLICATIONS

Michellys et al, J. Med. Chem. vol. 46, pp. 2683–2696 (2003).*
The Merck Manual, 16$^{th}$ ed. ® 1992 Merck & Co., Inc., pp. 1106–1125.*
Mangelsdorf et al. The Retinoid Receptors In: The Retinoids pp.: 319–349 (1994).
Dawson et al. Chemistry and Biology of Synthetic Retinoids pp.: 324–356 (1990).
Mukherjee et al. Nature vol. 386 pp.: 407–410 (1997).
Heyman et al. Cell vol. 68 pp.: 397–406 (1992).
Allegretto et al. Journal of Biological Chemistry vol. 268 pp.: 26625–26633 (1993).
Cheng et al. Biochemical Pharmacology vol. 22 pp.: 3099–3108 (1973).
Feigner et al. Focus vol. 11 pp.: 21–24 (1989).

* cited by examiner

Primary Examiner—Richard L. Raymond
Assistant Examiner—Zachary C. Tucker
(74) Attorney, Agent, or Firm—Gabor L. Szekeres

(57) ABSTRACT

Compounds of the formula

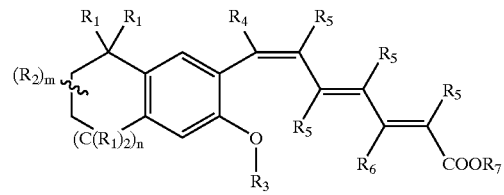

where the variables have the meaning defined in the specification are capable of reducing serum glucose levels in diabetic mammals without the undesirable side effect of reducing serum thyroxine levels.

20 Claims, No Drawings

5,6,7,8-TETRAHYDRONAPHTHALEN-2-YL-7-FLUOROALKYL-HEPTATRIENOIC ACID DERIVATIVES HAVING SERUM GLUCOSE REDUCING ACTIVITY

BACKGROUND OF THE INVENTION

Field of Invention

The present invention relates to compounds that have the property of reducing serum glucose and serum triglyceride levels in diabetic mammals without the undesirable properties of reducing serum thyroxine levels and transiently raising triglyceride levels. More particularly, the present invention relates to 5,6,7,8-tetrahydronaphthalen-2-yl 2,6-difluoroheptatrienoic acid derivatives having the above-noted biological property.

Compounds that have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

For a general overview of the retinoid receptors see Mangelsdorf et al. (1994) The Retinoid Receptors In: The Retinoids, edited by Sporn et al. p 319–349. Raven Press, Ltd., New York. For another general overview see Dawson and William H. Okamura, Chemistry and Biology of Synthetic Retinoids, published by CRC Press Inc., 1990, pages 324–356. The following further patents are of interest as background to the present invention: U.S. Pat. Nos. 5,721,103; 5,801,253; 6,326,397; PCT Publications WO 97/12853 and WO 01/19770.

Relatively recently it has become known that certain retinoid compounds are capable of reducing serum glucose levels in diabetic mammals. Mukherjee, R.; Davies, P. J.; Crombie, D. L. Bishoff, E. D.; Cesario, R. M.; Jow Hamann, L. G.; Boehm, M. F.; Mondon, C. E.; Nadzan, A. M.; Patemiti, J. R. Jr.; Heyman, R. A. Sensitization of Diabetic and Obese Mice to Insulin by Retinoid X Receptor Agonists. Nature 1997, 386 (6623), 407–410. The compound (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid, described in U.S. Pat. No. 6,114,533, has this property. A disadvantage of the prior art retinoid compounds that reduce serum glucose levels is that their administration usually also results in the pharmacologically undesirable reduction of serum thyroxine levels and a transient increase in serum triglyceride levels. The present invention is directed to novel compounds which do not have these undesirable side effects.

SUMMARY OF THE INVENTION

The present invention relates to compounds of Formula 1

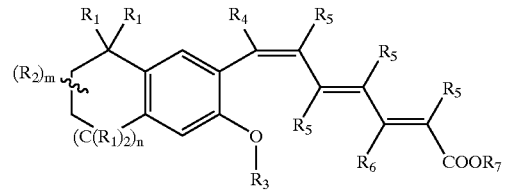

Formula 1 where m is an integer having the values of 0 to 4;
n is an integer having the values of 0 or 1;
$R_1$ is independently H, or alkyl of 1 to 6 carbons;
$R_2$ is independently H, alkyl of 1 to 6 carbons, F, Cl, Br or I;
$R_3$ is alkyl of 1 to 4 carbons, or $OCH_2OR_8$;
$R_4$ is fluoroalkyl having one to 4 carbons;
$R_5$ is H, F or Cl;
$R_6$ H or alkyl of 1 to 3 carbons, and
$R_7$ is H, alkyl of 1 to 6 carbons, $OCH_2OR_8$ or $OCH_2OCOR_8$ where $R_8$ is alkyl of 1 to 3 carbons, or a pharmaceutically acceptable salt of said compound.

The present invention also relates to pharmaceutical compositions incorporating the compounds of Formula 1 and to methods of treatment of diabetic mammals with pharmaceutical compositions containing one or more compounds of Formula 1 to reduce serum glucose levels in said mammals. The present invention also relates to the methods of using the compounds of the invention to treat diseases and conditions which are responsive to treatment by retinoids.

DETAILED DESCRIPTION OF THE INVENTION

General Embodiments and Synthetic Methodology
Definitions

The term alkyl refers to and covers any and all groups which are known as normal alkyl and branched-chain alkyl.

A pharmaceutically acceptable salt may be prepared for any compound in this invention having a functionality capable of forming a salt, for example an acid functionality. A pharmaceutically acceptable salt is any salt that retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The compounds of the present invention include olephinic double bonds about which trans and cis (E and Z) stereoisomerism can exist. The compounds of the present invention have the specific orientations of substituents relative to the double bonds as is indicated in the name of the respective compound, and/or by specific showing in the structural formula of the orientation of the substituents relative to the respective double bonds. Some of the compounds of the present invention may contain one or more chiral centers and therefore may exist in enantiomeric and diastereomeric forms. The scope of the present invention is intended to cover the trans and cis (E and Z) isomers as specifically shown and/or named, as well as pure enantiomers (optical isomers), diastereomers, mixtures of diastereomers and racemic mixtures of enantiomers.

Reaction Scheme 1 discloses a presently preferred synthetic route to compounds of the invention which are tetrahydronaphthalene derivatives (in Formula 1 the integer n=1). Although this synthetic route is general, the cis and/or trans isomerism of the compounds of the invention is indicated properly, the variable $R_5$ in positions 4,5 and 6 of the heptatrienoic acid moiety of Formula 1 is shown as hydrogen (H), as in the preferred embodiments. However, based on the present disclosure and general knowledge in the art those having ordinary skill in synthetic methodology can readily modify the herein described reactions to obtain all compounds within the scope of Formula 1, including those where the $R_5$ group in one or more of these positions is fluoro (F) or chloro.

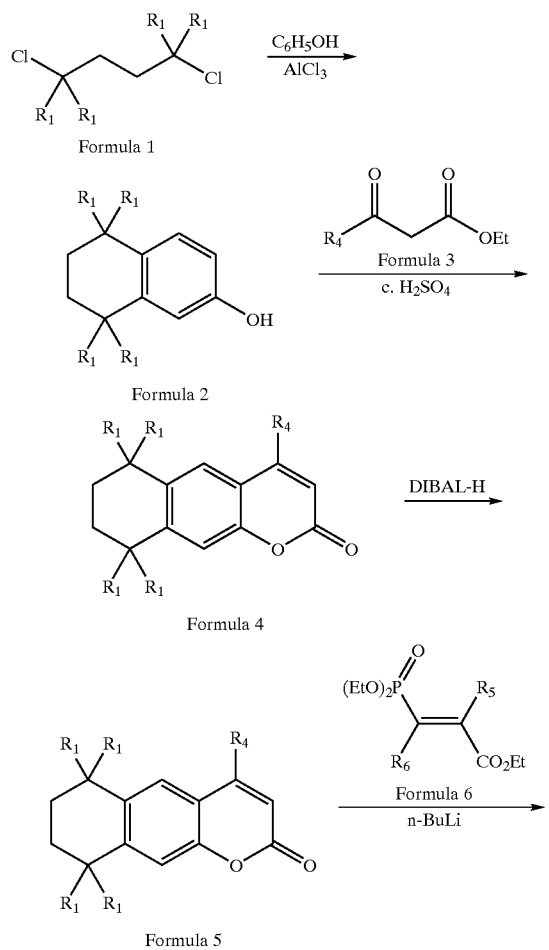

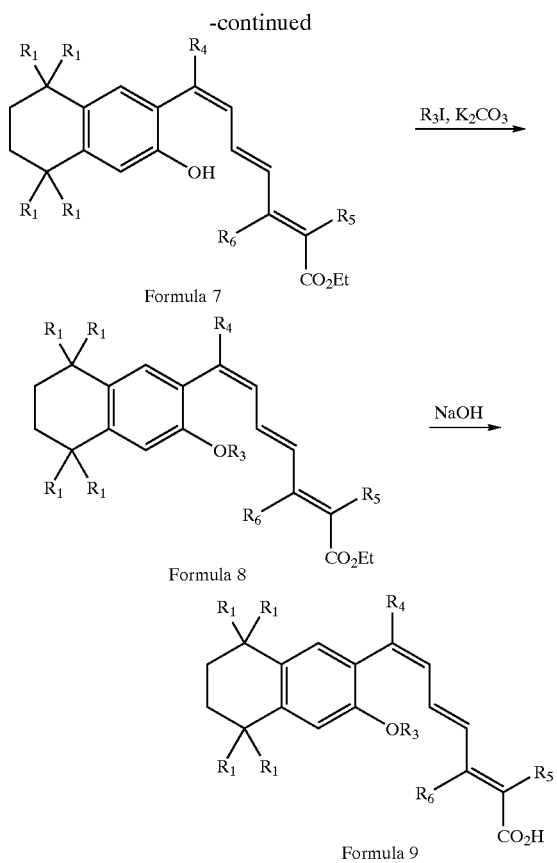

Referring now to Reaction Scheme 1 the starting material is a dichloroalkyl compound of Formula 1 that is already substituted with the $R_1$ groups. Such dichloro compounds are either available commercially, or can be prepared in accordance with the chemical scientific and patent literature, or by such modifications of known synthetic procedures that are readily apparent to those skilled in the art. An example for a compound in accordance with Formula 1 is 2,5-dichloro-2,5-dimethyl-hexane that serves as the starting material for the presently preferred compounds of the invention. 2,5-Dichloro-2,5-dimethyl-hexane can be obtained from 2,5-dimethyl-hexane-2,5-diol which is available commercially (Aldrich Chemical Co.). The dichloroalkyl compound of Formula 1 is reacted with phenol under Friedel Crafts conditions to provide a 3-hydroxy-tetrahydronaphthalene derivative of Formula 2. The 3-hydroxy-tetrahydronaphthalene derivative of Formula 2 is then reacted with a acetoacetate derivative of Formula 3, where the variable $R_4$ is defined as fluoroalkyl of 1 to 4 carbons, as in Formula 1. An example for the reagent of Formula 3 that is used for the synthesis of the presently preferred compounds of the invention is ethyl trifluoroacetoacetate. Reaction of the 3-hydroxy-tetrahydronaphthalene derivative of Formula 2 with the acetoacetate derivative of Formula 3 provides a benzo[g]chromen-2-one derivative of Formula 4, that is reduced with di-iso-butyl aluminum hydride (DIBAL-H) to the corresponding benzo[g]chromen-2-ol derivative of Formula 5. The benzo[g]chromen-2-ol derivative of Formula 5 is reacted under Horner Emmons conditions with a (diethoxyphosphoryl)-alkenoic acid ester of Formula 6 where the variables $R_5$ and $R_6$ are defined as in connection with Formula 1, to provide a 3-hydroxy-5,6,7,8-tetrahydronaphthalen-2-yl-heptatrienoic acid ester derivative of Formula 7. An example for the Horner Emmons reagent of Formula 6, that is used for the synthesis of the presently preferred compounds of the invention is 3-(diethoxy-phosphoryl)-but-2-enoic acid ethyl ester. The free hydroxyl group of 3-hydroxy-5,6,7,8-tetrahydronaphthalen-2-yl-heptatrienoic acid ester derivative of Formula 7 is then alkylated with a reagent, (such as $R_3I$) capable of introducing the $R_3$ group ($R_3$ is defined as in connection with Formula 1) to give a 3-alkoxy-5,6,7,8-tetrahydronaphthalen-2-yl-heptatrienoic acid ester derivative of Formula 8. The compounds of Formula 8 are within the scope of the invention. The ester group of the compounds of Formula 8 can be saponified to provide the free 3-alkoxy-5,6,7,8-tetrahydronaphthalen-2-yl-heptatrienoic acid derivatives, or their pharmaceutically acceptable salts of Formula 9. The compounds of Formula 9 are also within the scope of the present invention.

Reaction Scheme 2 illustrates a general route for the synthesis of compounds of the invention in which the variable n of Formula 1 is zero (0).

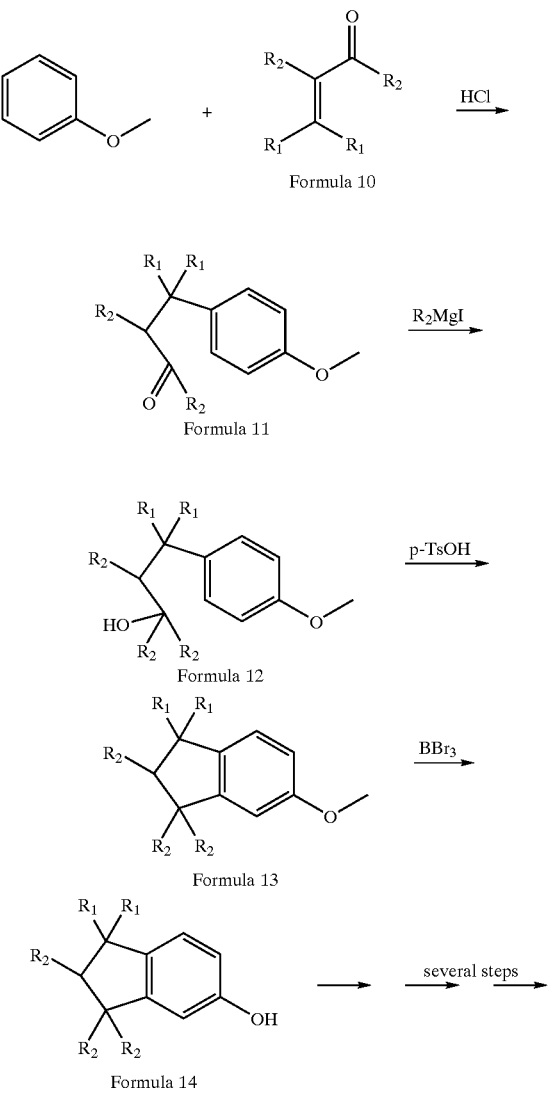

Reaction Scheme 2

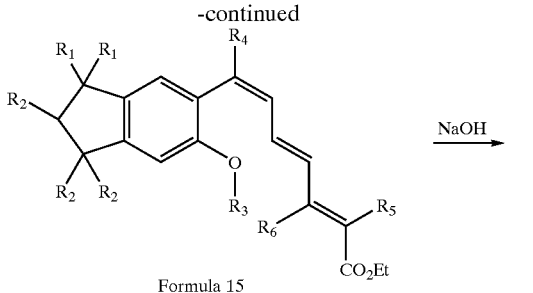

Formula 15

Formula 16

In accordance with this scheme, anisole is reacted in a Friedel Crafts type reaction with an enone of Formula 10. The enone of Formula 10 includes the substituents $R_1$ and $R_2$, which are defined as in connection with Formula 1. Preferably the $R_1$ and $R_2$ substituents in this scheme respectively represent methyl groups or hydrogen so as to give rise to indane derivatives of Formula 15 and of 16 that are substituted with two geminal dimethyl groups. The enones of Formula 10 are available commercially, or in accordance with the chemical scientific and patent literature, or by such modifications of known synthetic procedures that are readily apparent to those skilled in the art. An example for a compound in accordance with Formula 10 is 4-methyl-3-penten-2-one. Reaction of anisole with the enone of Formula 10 gives rise to the 4-methoxyphenyl-alkanone compound of Formula 11. The 4-methoxyphenyl-alkanone compound of Formula 11 is reacted with a Grignard reagent of the formula $R_2MgI$ where the variable $R_2$ represents an alkyl group as defined in Formula 1. The resulting alcohol of Formula 12 is cyclized by treatment with acid to give the methoxy substituted indane derivative of Formula 13. The methoxy substituted indane derivative of Formula 13 is reacted with boron tribromide to remove the methoxy group and to yield the hydroxy substituted indane derivative of Formula 14. The compound of Formula 14 is subjected to a series of reaction analogous to the reactions described in Reaction Scheme 1 (starting with Formula 2), to provide the indane substituted heptatrienoic acid ester (Formula 15) and indane substitituted heptatrienoic acid (Formula 16) derivatives, both of which are compounds of the invention within the scope of Formula 1.

Specific Embodiments of the Compounds of the Invention

Referring now to Formula 1, the presently preferred compounds of the invention are tetrahydronaphthalene derivatives (n of Formula 1 represents the integer one (1)).

In the preferred compounds of the invention the variable $R_1$ represents alkyl groups of 1 to 3 carbons, and even more preferably methyl. Still more preferably the tetrahydronaphthalene group is substituted in the 5 and 8 positions by geminal dimethyl groups and still further substitution of the non-aromatic portion by additional $R_2$ groups is presently not preferred. The $R_3$ group of the preferred compounds is methyl, ethyl, or n-propyl. The variable $R_4$ of the preferred compounds is trifluoromethyl, and $R_5$ is preferably hydrogen (H). $R_6$ is preferably methyl, and $R_7$ is preferred as H, or alkyl of 1 to 3 carbons or methoxymethyl, or as a pharmaceutically acceptable salt of the carboxylic acid. Still more preferably $R_7$ is H (or a salt of the carboxylic acid) or ethyl.

The synthesis of the presently most preferred compounds of the invention is shown in Reaction Scheme 3 and a detailed description of the experimental procedures for synthesizing these most preferred exemplary compounds is also provided below.

trated in vacuo. Recrystallization of the resulting solid residue from $Et_2O$ gave the title compound as white crystals (216 g, 85%).

$^1$H NMR (300 MHz, $CDCl_3$): δ 1.60 (s, 12H), 1.95 (s, 4H).

5,5,8,8-Tetramethyl-5,6,7,8-tetrahydro-naphthalen-2-ol (Intermediate 2)

To a solution of 2,5-dichloro-2,5-dimethyl-hexane (Intermediate 1, 97 g, 0.53 mol) and phenol (50 g, 0.53 mol) in $CHCl_3$ (500 mL) at 0° C. was added $AlCl_3$ (71 g, 0.54 mmol) portionwise. After stirring for 2 h at 0° C., the mixture was poured onto ice and was extracted with $Et_2O$.

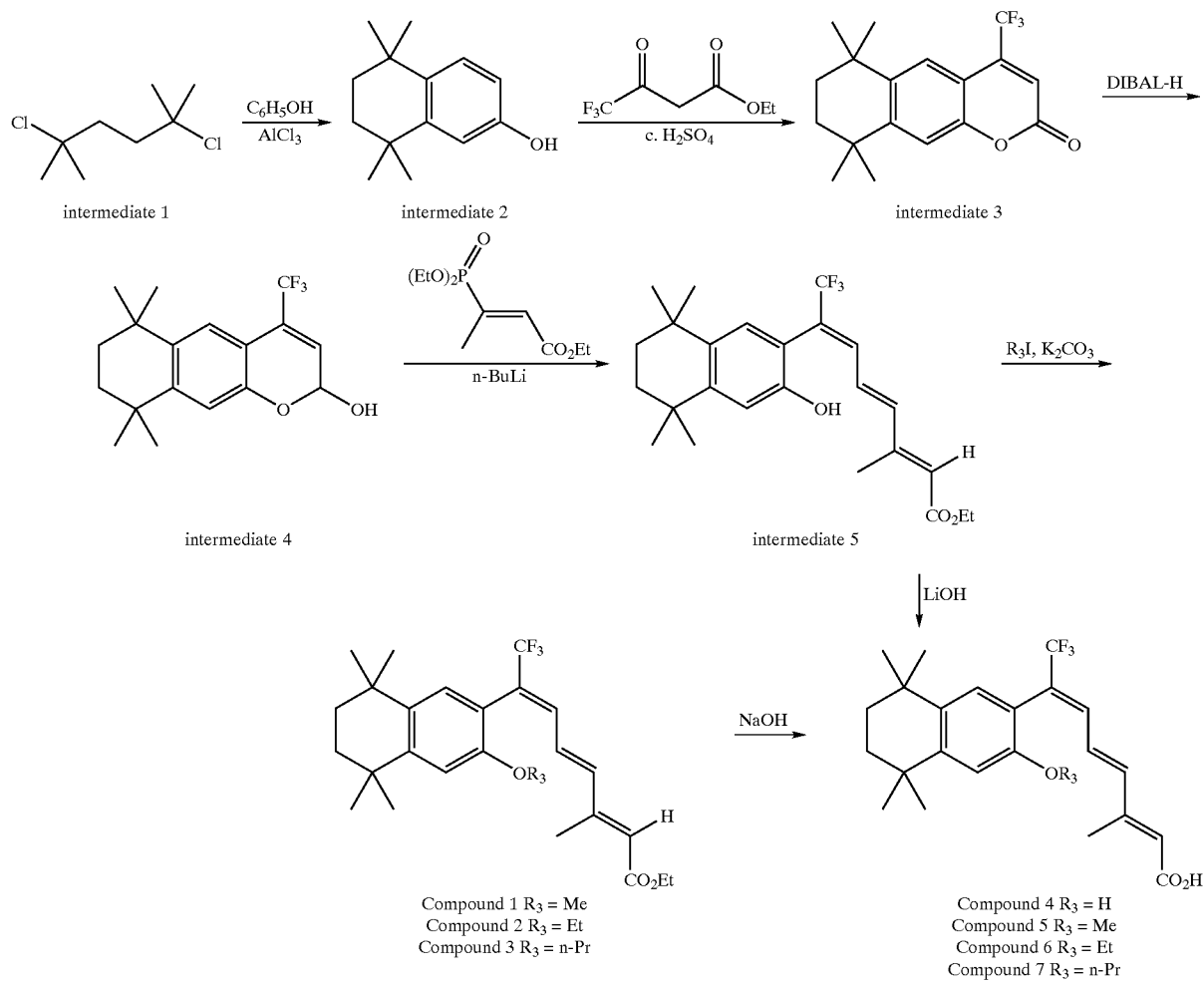

Reaction Scheme 3

Experimental Procedures For Synthesizing the Exemplary Compounds of the Invention

2,5-Dichloro-2,5-dimethyl-hexane (Intermediate 1)

Concentrated HCl (1.2 L, 14.4 mol) was added to commercial 2,5-dimethyl-hexane-2,5-diol (202 g, 1.4 mol) and the slurry was stirred at ambient temperature for 1.5 h. The mixture was filtered. The collected solid was washed with water (×3), dissolved in $Et_2O$, washed successively with $H_2O$, $NaHCO_3$, and brine, dried over $Na_2SO_4$, and concen- The organic layer was washed with brine, dried over $Na_2SO_4$, and concentrated in vacuo. Recrystallization of the resulting solid from $Et_2O$-hexane (1:1) gave the title compound as off-white crystals (95.7 g, 89%).

$^1$H NMR (300 MHz, $CDCl_3$):δ1.25 (s, 6H), 1.26 (s, 6H), 1.66 (s, 4H), 4.50 (s, 1H), 6.62 (dd, J=9.0, 3.0 Hz, 1H), 6.76 (d, J=3.0 Hz, 1H), 7.17 (d, J=9.0 Hz, 1H).

6,6,9,9-Tetramethyl-4-trifluoromethyl-6,7,8,9-tetrahydro-benzo[g]chromen-2-one (Intermediate 3)

A mixture of 5,5,8,8-tetramethyl-5,6,7,8-tetrahydro-naphthalen-2-ol (Intermediate 2, 4.12 g, 20.2 mmol), ethyl trifluoroacetoacetate (7.4 mL, 50.4 mmol), and $H_2SO_4$ (8 mL, 75%) was heated at 100° C. for 4 h. The mixture was poured onto ice, quenched with $NaHCO_3$ and extracted with $Et_2O$. The organic layer was washed with brine, dried over $Na_2SO_4$, and concentrated in vacuo. The residue was dissolved in $Et_2O$, a readily crystalline side product precipitated and was removed by filtration. The filtrate was concentrated to give a residue. Recrystallization of the residue gave the title compound as white crystals (2.5 g, 38%).

$^1$H NMR (300 MHz, $CDCl_3$):δ1.31 (s, 12H), 1.72 (s, 4H), 6.70 (d, J=0.6 Hz, 1H), 7.32 (s, 1H), 7.62 (q, J=2.1 Hz, 1H).

6,6,9,9-Tetramethyl-4-trifluoromethyl-6,7,8,9-tetrahydro-2H-benzo[g]chromen-2-ol (Intermediate 4)

To a solution of 6,6,9,9-tetramethyl-4-trifluoromethyl-6,7,8,9-tetrahydro-benzo[g]chromen-2-one (Intermediate 3, 348 mg, 1.07 mmol) in $CH_2Cl_2$ (5 mL) at −78° C. was added di-iso-butyl aluminum hydride (DIBAL-H, 1.40 mL, 1.0 M in $CH_2Cl_2$) over 10 min. After stirring at −78° C. for 3 h, the reaction was quenched with aqueous $NH_4Cl$, followed by 1M HCl, and the aqueous layer was extracted with $Et_2O$ (×3). The combined organic layers were washed with brine, dried over $Na_2SO_4$, and concentrated in vacuo. The residue was purified by flash column chromatography on silica gel (10% EtOAc-hexane) to give the title compound as a clear oil (346 mg, 99%) that was used directly in the next reaction.

(2E,4E,6Z)-8,8 8-Trifluoro-7-(3-hydroxy-5,5,8,8-tetramethyl-5,6,7,8-tetrahydro-naphthalen-2-yl)-3-methyl-octa-2,4,6-trienoic acid ethyl ester (Intermediate 5)

To a solution of 3-(diethoxy-phosphoryl)-but-2-enoic acid ethyl ester (0.9 mL, 3.7 mmol) in 1,3-dimethyl-3,4,5,6-tetrahydro-2(1H)-pyrimidinone (DMPU, 4 mL) and tetrahydrofuran (THF, 8 mL) at −78° C. was added n-BuLi (2.3 mL, 1.6 M in hexane) dropwise. After 10 min, a solution of crude 6,6,9,9-tetramethyl-4-trifluoromethyl-6,7,8,9-tetrahydro-2H-benzo[g]chromen-2-ol (Intermediate 4, 346 mg, 1.06 mmol) in THF (5 mL) was added via cannula. The reaction was gradually warmed to ambient temperature overnight and was found by TLC analysis to be complete. The reaction was quenched with aqueous $NH_4Cl$ and extracted with EtOAc (×3). The combined organic layers were washed with brine, dried over $Na_2SO_4$, and concentrated in vacuo. The residue was purified by flash column chromatography on silica gel (10% EtOAc-hexane) to give a 2:1 mixture of the title compound and its 13-Z isomer (292 mg). Further purification by HPLC (10% EtOAc-hexane) afforded the title compound as a white solid (183 mg, 40%).

$^1$H NMR (300 MHz, $CDCl_3$): δ 1.24 (s, 6H), 1.28 (s, 6H), 1.29 (t, J=7.2 Hz, 3H), 1.68 (s, 4H), 2.14 (d, J=1.2 Hz, 3H), 4.17 (q, J=7.2Hz, 2H), 4.76 (br s, 1H), 5.87 (s, 1H), 6.34 (dd, J=15.3, 11.1 Hz, 1H), 6.58 (d, J=15.3 Hz, 1H), 6.86 (s, 1H), 7.03 (s, 1H), 7.04 (dd, J=10.8, 1.2 Hz, 1H).

General Procedure A

(2E,4E,6Z)-8,8,8-Trifluoro-7-(3-methoxy-5,5,8,8-tetramethyl-5,6,7,8-tetrahydro-naphthalen-2-yl)-3-methyl-octa-2,4,6-trienoic acid ethyl ester (Compound 1)

A mixture of (2E,4E,6Z)-8,8,8-trifluoro-7-(3-hydroxy-5,5,8,8-tetramethyl-5,6,7,8-tetrahydro-naphthalen-2-yl)-3-methyl-octa-2,4,6-trienoic acid ethyl ester (Intermediate 5, 160 mg, 0.37 mmol), $K_2CO_3$ (253 mg, 1.83 mmol), MeI (0.12 mL, 1.83 mmol), and acetone (2 mL), was stirred at ambient temperature for overnight. The reaction mixture was diluted with EtOAc, washed with brine, dried over $Na_2SO_4$, and concentrated in vacuo. The residue was purified by flash column chromatography on silica gel (3% EtOAc-hexane) to produce the title compound and its 2-Z isomer as a 2:1 mixture (167 mg). Further purification by HPLC (2.5% EtOAc-hexane) afforded the title compound as a clear oil (87 mg, 53%).

$^1$H NMR (300 MHz, $CDCl_3$):δ1.25 (s, 6H), 1.30 (t, J=7.2 Hz, 3H), 1.34 (s, 6H), 1.71 (s, 4H), 2.15 (d, J=1.2 Hz, 3H), 3.78 (s, 1H), 4.18 (q, J=7.1 Hz, 2H), 5.85 (s, 1H), 6.38 (dd, J=15.3, 10.8 Hz, 1H), 6.51 (d, J=15.3 Hz, 1H), 6.85 (s, 1H), 6.93 (dd, J=10.8, 1.2 Hz, 1H), 7.05 (s, 1H).

(2E,4E,6Z)-7-(3-Ethoxy-5,5,8,8-tetramethyl-5,6,7,8-tetrahydro-naphthalen-2-yl)-8,8,8-trifluoro-3-methyl-octa-2,4,6-trienoic acid ethyl ester (Compound 2)

Following General Procedure A and using (2E,4E,6Z)-8,8,8-trifluoro-7-(3-hydroxy-5,5,8,8-tetramethyl-5,6,7,8-tetrahydro-naphthalen-2-yl)-3-methyl-octa-2,4,6-trienoic acid ethyl ester (Intermediate 5, 160 mg, 0.37 mmol), $K_2CO_3$ (253 mg, 1.83 mmol), EtI (0.15 mL, 1.83 mmol), and acetone (2 mL) followed by HPLC (2.5% EtOAc-hexane), the title compound was obtained as a clear syrup (81 mg, 48%).

$^1$H NMR (300 MHz, $CDCl_3$):δ1.25 (s, 6H), 1.30 (t, J=7.2 Hz, 3H), 1.32 (t, J=6.9 Hz, 3H), 1.32 (2 s, 6H), 1.70 (s, 4H), 2.15 (d, J=1.2 Hz, 3H), 4.01 (q, J=6.9 Hz, 2H), 4.18 (q, J=7.1 Hz, 2H), 5.85 (s, 1H), 6.40 (dd, J 15.3, 10.5 Hz, 1H), 6.51 (d, J=15.6 Hz, 1H), 6.83 (s, 1H), 6.91 (dd, J=9.9, 1.2 Hz, 1H), 7.05 (s, 1H).

(2E,4E,6Z)-8,8,8-Trifluoro-3-methyl-7-(5 ,5,88-tetramethyl-3-propoxy-5,6,7,8-tetrahydro-naphthalen-2-yl)-octa-2,4,6-trienoic acid ethyl ester (Compound 3)

Following General Procedure A and using (2E,4E,6Z)-8,8,8-trifluoro-7-(3-hydroxy-5,5,8,8-tetramethyl-5,6,7,8-tetrahydro-naphthalen-2-yl)-3-methyl-octa-2,4,6-trienoic acid ethyl ester (Intermediate 5, 160 mg, 0.37 mmol), $K_2CO_3$ (253 mg, 1.83 mmol), PrI (0.18 mL, 1.83 mmol), and acetone (2 mL) followed by HPLC (2.5% EtOAc-hexane), the title compound was obtained as a clear syrup (83 mg, 47%).

$^1$H NMR (300 MHz, $CDCl_3$):δ0.95 (t, J=7.2 Hz, 3H), 1.23 (s, 6H), 1.28 (t, J=7.0 Hz, 3H), 1.31 (s, 6H), 1.69 (s, 4H), 1.72 (m, 2H), 2.13 (d, J=1.2 Hz, 3H), 3.87 (t, J=6.3 Hz 2H), 4.17 (q, J=7.1 Hz, 2H), 5.83 (s, 1H), 6.39 (dd, J=15.5, 10.3 Hz, 1H), 6.49 (d, J=15.5 Hz, 1H), 6.80 (s, 1H), 6.90 (dq, J=10.3, 1.5 Hz, 1H), 7.03 (s, 1H).

(2E,4E,6Z)-8,8,8-Trifluoro-7-(3-hydroxy-5,5,8,8-tetramethyl-5,6,7,8-tetrahydro-naphthalen-2-yl)-3-methyl-octa-2,4,6-trienoic acid (Compound 4)

To a solution of (2E,4E,6Z)-8,8,8-trifluoro-7-(3-hydroxy-5,5,8,8-tetramethyl-5,6,7,8-tetrahydro-naphthalen-2-yl)-3-methyl-octa-2,4,6-trienoic acid ethyl ester (Intermediate 5, 100 mg, 0.23 mmol) in EtOH-THF-$H_2O$ (2 mL, 2 mL, 0.3 mL) was added LiOH.$H_2O$ 29 mg, 0.69 mmol). The mixture was heated to 40° C. for 4 h and was cooled to ambient temperature, acidified with 1M HCl and extracted with EtOAc (×3). The combined organic layers were washed with brine, dried over $Na_2SO_4$, and concentrated in vacuo. The residue was purified by flash column chromatography on silica gel (40% EtOAc-hexane) to give a 3:2 mixture of the title compound and its 13-Z isomer (91 mg). Further purification by HPLC (20% EtOAc-hexane) afforded the title compound as a white solid (39 mg, 42%).

$^1$H NMR (300 MHz, CDCl$_3$):δ1.25 (s, 6H), 1.30 (s, 6H), 1.70 (s, 4H), 2.17 (s, 3H), 5.90 (s, 1H), 6.41 (dd, J=15.3, 11.1 Hz, 1H), 6.61 (d, J=15.3Hz, 1H), 6.88 (s, 1H), 7.05 (s, 1H), 7.06 (br d, J=9.6 Hz, 1H).

General Procedure B (2E,4E,6Z)-8,8,8-Trifluoro-7-(3-methoxy-5,5,8,8-tetramethyl-5,6,7,8-tetrahydro-naphthalen-2-yl)-3-methyl-octa-2,4,6-trienoic acid (Compound 5)

To a solution of (2E,4E,6Z)-8,8,8-trifluoro-7-(3-methoxy-5,5,8,8-tetramethyl-5,6,7,8-tetrahydro-naphthalen-2-yl)-3-methyl-octa-2,4,6-trienoic acid ethyl ester (Compound 1, 87 mg, 0.19 mmol) in EtOH (2 mL) was added 1M NaOH (0.68 mL). The mixture was heated to 60° C. for 2 h, was cooled to ambient temperature, acidified with 1M HCl, and extracted with EtOAc (×3). The combined organic layers were washed with brine, dried over Na$_2$SO$_4$, and concentrated in vacuo. The residue was purified by flash column chromatography on silica gel (40% EtOAc-hexane) and HPLC (20% EtOAc-hexane) to give the title compound as a white solid (75 mg, 92%).

$^1$H NMR (300 MHz, CDCl$_3$):δ1.25 (s, 6H), 1.34 (s, 6H), 1.70 (s, 4H), 2.15 (d, J=0.9 Hz, 3H), 3.78 (s, 3H), 5.87 (s, 1H), 6.42 (dd, J=15.3, 10.8 Hz, 1H), 6.54 (d, J=15.5 Hz, 1H), 6.85 (s, 1H), 6.94 (dd, J=10.8, 1.5 Hz, 1H), 7.05 (s, 1H).

(2E,4E,6Z)-7-(3-Ethoxy-5,5,8,8-tetramethyl-5,6,7 8-tetrahydro-naphthalen-2-yl)-8,8,8-trifluoro-3-methyl-octa-2,4,6-trienoic acid (Compound 6)

Following General Procedure B and using (2E,4E,6Z)-7-(3-ethoxy-5,5,8,8-tetramethyl-5,6,7,8-tetrahydro-naphthalen-2-yl)-8,8,8-trifluoro-3-methyl-octa-2,4,6-trienoic acid ethyl ester (Compound 2, 81 mg, 0.18 mmol), 1M NaOH (0.61 mL), and EtOH (3 mL) at 60° C. for 1 h followed by flash column chromatography on silica gel (30% EtOAc-hexane) and HPLC (15% EtOAc-hexane), the title compound was obtained as a white solid (75 mg, 99%).

$^1$H NMR (300 MHz, CDCl$_3$):δ1.25 (s, 6H), 1.30 (t, J=7.2 Hz, 3H), 1.31 (2 s, 6H), 1.69 (m, 4H), 2.16 (s, 3H), 4.01 (m, 2H), 5.87 (s, 1H), 6.47 (dd, J=15.0, 10.0 Hz, 1H), 6.53 (d, J=15.0 Hz, 1H), 6.83 (s, 1H), 6.92 (dd, J=10.0, 1.5 Hz, 1H), 7.05 (s, 1H).

(2E,4E,6Z)-8,8,8-Trifluoro-3-methyl-7-(5,5,8,8-tetramethyl-3-propoxy-5,6,7,8-tetrahydro-naphthalen-2-yl)-octa-2,4,6-trienoic acid (Compound 7)

Following General Procedure B and using (2E,4E,6Z)-8,8,8-trifluoro-3-methyl-7-(5,5,8,8-tetramethyl-3-propoxy-5,6,7,8-tetrahydro-naphthalen-2-yl)-octa-2,4,6-trienoic acid ethyl ester (Compound 3, 83 mg, 0.17 mmol), 1M NaOH (0.35 mL), and EtOH (3 mL) at 60° C. for 1.5 h followed by flash column chromatography on silica gel (30% EtOAc-hexane) and HPLC (15% EtOAc-hexane), the title compound was obtained as a white solid (60 mg, 77%).

$^1$H NMR (300 MHz, CDCl$_3$):δ0.97 (t, J=7.2 Hz, 3H), 1.26 (s, 6H), 1.34 (br s, 6H), 1.69 (s, 4H), 1.71 (s, 2H), 1.73 (m, 2H), 2.17 (d, J=0.9 Hz, 3H), 3.90 (t, J=6.3 Hz 2H), 5.88 (s, 1H), 6.47 (dd, J=15.3, 9.9 Hz, 1H), 6.54 (d, J 15.6 Hz, 1H), 6.84 (s, 1H), 6.93 (dq, J=9.9, 1.5 Hz, 1H), 7.06 (s, 1H).

Biological Activity, Modes of Administration

It has been discovered in accordance with the present invention that compounds of this invention are capable of significantly reducing serum glucose levels and reducing or maintaining serum triglyceride levels in diabetic mammals, without the undesirable side effects of reducing serum thyroxine levels (hypothyroidism) and transiently raising triglyceride levels (hypertriglyceridemia). The compounds of the invention are partial agonists of the RXRs. Table 1 below discloses the results of certain assays where the compounds of the invention were tested as agonists of RAR and RXR retinoid receptors.

One such assay is a chimeric receptor transactivation assay which tests for agonist-like activity in the RAR$_\alpha$, RAR$_\beta$ and RAR$_\gamma$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in EC$_{50}$ numbers, as they are also in the chimeric receptor transactivation assay. The results of the ligand binding assay are expressed in K$_i$ numbers. (See Cheng et al. Biochemical Pharmacology Vol. 22 pp 3099–3108, expressly incorporated herein by reference.)

Efficacy in a transactivation assay is expressed as a percentage of the maximum potency attained by the compound compared to a standard which, in this case, is the compound named (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid. This standard compound is described in U.S. Pat. No. 6,114,533.

Table 1 discloses the activity of certain exemplary compounds of the invention in the above-described receptor transactivation and binding assays. Particularly, the transactivation data pertaining to activation of the RAR receptors were obtained in the chimeric assay, and the transactivation data pertaining to the activation of RXR receptors were obtained in the holoreceptor assay. In the chimeric receptor transactivation assay the compounds were essentially inactive in activating RAR$_\alpha$, RAR$_\beta$ and RAR$_\gamma$ receptors.

TABLE 1

| compound Number | Structure | RAR Trans. EC₅₀ (nM) / RAR Binding Kᵢ (nM) | | | RXR Trans. EC₅₀ (nM) / RXR Binding Kᵢ (nM) | | |
|---|---|---|---|---|---|---|---|
| | | α | β | γ | α | β | γ |
| 4 | (structure) | NA 2.4K | >0.5 K (~30) 4.4K | >0.5k (~30) 496 | 9 (65) 471 | 67 (54) 2.6K | 16 (69) ND |
| 5 | (structure) | NA 504 | 150 (32) 484 | NA 1.2K | 0.6 (112) 66 | 5 (111) 423 | 2 (121) ND |
| 6 | (structure) | NA >10 K | 67 (15) 372 | NA >10K | 10 (17) 14 | 97 (30) 68 | 25 (17) ND |
| 7 | (structure) | NA 1.8K | 54 (9) 452 | NA >10K | NA 22 | NA 115 | NA ND |

In Table 1, NA stands for not active at all as an agonist and ND stands for not determined. The first row of numbers pertaining to each compound is the measured EC₅₀ number. The second row of numbers indicates efficacy as a percentage compared to the standard compound, (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid. The third row of numbers pertaining to each compound is the binding $K_i$ number.

An assay described below tests the effect of compounds of the invention on serum glucose, tryglyceride and thyroxine levels in female 9–10 weeks old db/db mice.

Description of Assay.

Female diabetic db/db (9–10 weeks old) mice were maintained on standard laboratory food and treated by oral gavage with vehicle (corn oil), standard compound (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid (5 mg/kg) or the test compound (5-100 mg/kg, as described in Table 2) daily for seven days at 8:00 AM. Blood samples (70 μl) were taken by orbital bleeding at 11:00 AM on day 0 (pre-treatment), day 3, and day 6. On day 7, a blood sample (700 μl) was taken at 11:00 AM and the animals were sacrificed. Glucose, triglyceride and thyroxine (T4) levels were determined on a Boehringer Manheim Hatachi Clinical Chemistry Analyzer using standard protocols provided by the manufacturer and reagents that were supplied in commercially available kits (glucose and T4: Boehringer Manheim; triglycerides: Roche Diagnostics). A NUMBER OF animals were treated in each group. The results of the assays are summarized in Table 2.

TABLE 2

Glucose, Triglycerides, and Thyroxine (T4) in Female db/db mice (9–10 weeks old) treated with Vehicle, Standard Compound and Compound 6.

| Treatment (dose) | Glucose (mg/dl) | | | Triglycerides (mg/dl) | | T4 ($\mu$g/dL) |
|---|---|---|---|---|---|---|
| | Day 0 | Day 3, 3 h | Day 6, 3 h | Day 0 | Day 3, 3 h | Day 7 |
| Vehicle (Corn oil) | 541 ± 120 | 509 ± 64 | 581 ± 152 | 279 ± 105 | 420 ± 229 | 2.5 ± 0.4 |
| Standard compound (5 mg/kg) | 526 ± 135 | 444 ± 125 | 399 ± 128 | 290 ± 55 | 590 ± 422 | 1.5 ± 0.6 |
| Compound 6 (50 mg/kg) | 561 ± 159 | 442 ± 164 | 483 ± 175 | 350 ± 69 | 240 ± 192 | 2.5 ± 0.5 |

As the data indicate, the compounds of the invention not only cause significant decrease in serum glucose levels and maintain or reduce triglyceride levels in diabetic mammals, but in contrast with the prior art standard compound (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid do not have the undesirable side effect of reducing serum thyroxine levels.

Modes of Administration, Dosing

To treat diabetic mammals, including humans for the purpose of reducing serum glucose levels in said mammals a pharmaceutical composition containing one or more compound of the invention is administered to the mammal in daily doses in the range of 1 to 100 mg per kg body weight of the mammal. Preferably the daily dose is between 10 to 50 mg per kg body weight of the mammal.

Generally speaking the compounds of the invention are also useful for preventing or treating diseases and conditions that are responsive to compounds that promote the expression of or bind to receptors belonging to the steroid or thyroid receptor superfamily. More specifically the compounds of the invention can be used for preventing or treating skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of metabolic diseases and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA).

Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

To treat diabetes the compounds of this invention are preferably administered, orally.

For the prevention or treatment of other diseases or conditions the compounds of the invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 1 and 50 mg per kg of body weight per day would be expected to effect a therapeutic result in the treatment of many diseases for which these compounds are useful.

What is claimed is:

1. A compound of the formula

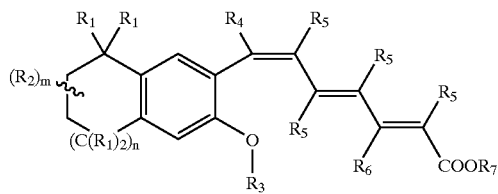

where m is an integer having the values of 0 to 4;

n is an integer having the values of 0 or 1;

$R_1$ is independently H, or alkyl of 1 to 6 carbons;

$R_2$ is independently H, alkyl of 1 to 6 carbons, F, Cl, Br or I;

$R_3$ is alkyl of 1 to 4 carbons, or $OCH_2OR_8$;

$R_4$ is fluoroalkyl having one to 4 carbons;

$R_5$ is H, F or Cl;

$R_6$ H or alkyl of 1 to 3 carbons, and $R_7$ is H, alkyl of 1 to 6 carbons, $CH_2OR_8$ or $CH_2OCOR_8$ where $R_8$ is alkyl of 1 to 3 carbons, or a pharmaceutically acceptable salt of said compound.

2. A compound in accordance with claim 1 where n is 1.

3. A compound in accordance with claim 1 where n is 0.

4. A compound in accordance with claim 1 where $R_1$ is alkyl of 1 to 3 carbons.

5. A compound in accordance with claim 1 where $R_3$ is methyl, ethyl, or n-propyl.

6. A compound in accordance with claim 1 where $R_4$ is trifluoromethyl.

7. A compound in accordance with claim 1 where $R_5$ is hydrogen.

8. A compound of the formula

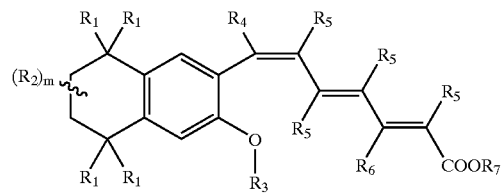

where m is an integer having the values of 0 to 4;

$R_1$ is independently alkyl of 1 to 3 carbons;

$R_2$ is independently H, alkyl of 1 to 6 carbons, F, Cl, Br or I;

$R_3$ is alkyl of 1 to 3 carbons;

$R_4$ is fluoroalkyl having one to 4 carbons;

$R_5$ is H, F or Cl;

$R_6$ H or alkyl of 1 to 3 carbons, and $R_7$ is H, alkyl of 1 to 6 carbons, $CH_2OR_8$ or $CH_2OCOR_8$ where $R_8$ is alkyl of 1 to 3 carbons, or a pharmaceutically acceptable salt of said compound.

9. A compound in accordance with claim 8 where m is zero (0).

10. A compound in accordance with claim 9 where $R_7$ is H, ethyl or methoxymethyl, or a pharmaceutically acceptable salt of said compound.

11. A compound of the formula

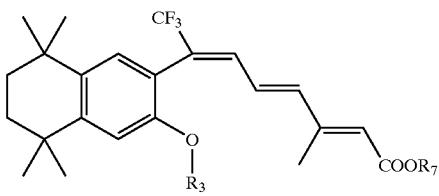

where $R_3$ is methyl, ethyl or n-propyl;

$R_7$ is H, alkyl of 1 to 6 carbons, $CH_2OR_8$ or $CH_2OCOR_8$ where $R_8$ is alkyl of 1 to 3 carbons, or a pharmaceutically acceptable salt of said compound.

12. A compound in accordance with claim 11 where $R_3$ is methyl.

13. A compound in accordance with claim 12 where $R_7$ is H or a pharmaceutically acceptable salt of said compound.

14. A compound in accordance with claim 11 where $R_3$ is ethyl.

15. A compound in accordance with claim 14 where $R_7$ is H or a pharmaceutically acceptable salt of said compound.

16. A compound in accordance with claim 11 where $R_3$ is n-propyl.

17. A compound in accordance with claim 16 where $R_7$ is H or a pharmaceutically acceptable salt of said compound.

18. A process for the treatment of non-insulin dependent diabetes in a mammal comprising administering to said mammal a blood glucose reducing amount of a compound of the formula

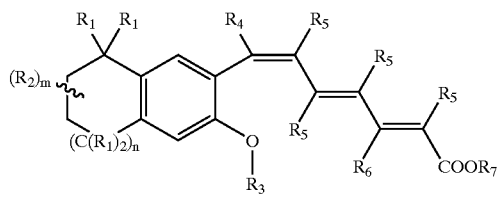

where m is an integer having the values of 0 to 4;

n is an integer having the values of 0 or 1;

$R_1$ is independently H, or alkyl of 1 to 6 carbons;

$R_2$ is independently H, alkyl of 1 to 6 carbons, F, Cl, Br or I;

$R_3$ is alkyl of 1 to 4 carbons, or $OCH_2OR_8$;

$R_4$ is fluoroalkyl having one to 4 carbons;

$R_5$ is H, F or Cl;

$R_6$ H or alkyl of 1 to 3 carbons, and $R_7$ is H, alkyl of 1 to 6 carbons, $CH_2OR_8$ or $CH_2OCOR_8$ where $R_8$ is alkyl of 1 to 3 carbons, or a pharmaceutically acceptable salt of said compound.

19. A process in accordance with claim 18 where the compound used in the process is in accordance with the formula

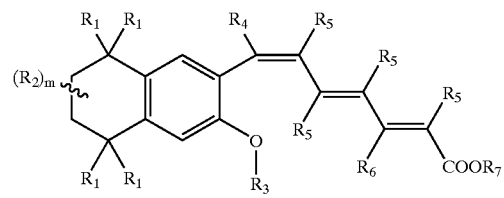

where $R_3$ is alkyl of 1 to 3 carbons, or a pharmaceutically acceptable salt of said compound.

20. A process in accordance with claim 18 where the compound used in the process is in accordance with the formula

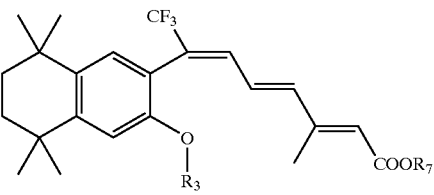

where $R_3$ is methyl, ethyl or n-propyl, and $R_7$ is H, alkyl of 1 to 6 carbons, $CH_2OR_8$ or $CH_2OCOR_8$ or a pharmaceutically acceptable salt of said compound.

* * * * *

UNITED STATES PATENT AND TRADEMARK OFFICE
CERTIFICATE OF CORRECTION

PATENT NO. : 6,884,820 B2
DATED : April 26, 2005
INVENTOR(S) : Beard et al.

It is certified that error appears in the above-identified patent and that said Letters Patent is hereby corrected as shown below:

Column 3,
Reaction scheme 1, formula 5, "double bond O" should be -- OH --.

Column 10,
Line 35, "(5,5,88" should be -- 5,5,8,8 --.

Columns 13-14,
Compound no. 4-7, table 1,

"
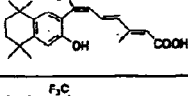
"

should be

UNITED STATES PATENT AND TRADEMARK OFFICE
CERTIFICATE OF CORRECTION

PATENT NO. : 6,884,820 B2
DATED : April 26, 2005
INVENTOR(S) : Beard et al.

It is certified that error appears in the above-identified patent and that said Letters Patent is hereby corrected as shown below:

Columns 13-14 (cont'd),

TABLE 1

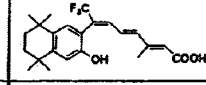

Column 17,
Line 50, "OCH$_2$OR$_8$" should be -- CH$_2$OR$_8$ --.

Column 19,
Line 17, "OCH$_2$OR$_8$" should be -- CH$_2$OR$_8$ --.

Signed and Sealed this

Fourteenth Day of February, 2006

JON W. DUDAS
*Director of the United States Patent and Trademark Office*

Disclaimer

6,884,820—Richard L. Beard, Newport Beach, CA (US); Haiqing Yuan, Irvine, CA (US); Roshantha A. Chandratratna, Laguna Hills, CA (US). 5,6,7,8-TETRAHYDRONAPHTHALEN-2YL-7-FLUOROALKYL-HEPTATRIENOIC ACID DERIVATIVES HAVING SERUM GLUCOSE REDUCING ACTIVITY. Patent dated April 26, 2005. Disclaimer filed August 8, 2011, by the assignee, Allergan, Inc., Irvine, CA (US).

Hereby disclaims all of the claims 1-20 of said patent.

*(Official Gazette November 22, 2011)*